US006405085B1

(12) United States Patent
Graupner et al.

(10) Patent No.: US 6,405,085 B1
(45) Date of Patent: Jun. 11, 2002

(54) METHOD FOR DETERMINING A VARIABLE CONTROL PARAMETER FOR AN IMPLANTABLE MEDICAL DEVICE

(75) Inventors: Harald Graupner, Erlangen; Michael Lippert, Ansbach, both of (DE)

(73) Assignee: Biotronik Mess- und Therapiegerate GmbH & Co. Ingenieurbüro Berlin, Berlin (DE)

( * ) Notice: Subject to any disclaimer, the term of this patent is extended or adjusted under 35 U.S.C. 154(b) by 40 days.

(21) Appl. No.: 09/599,257

(22) Filed: Jun. 23, 2000

(30) Foreign Application Priority Data

Jun. 23, 1999 (DE) .......................................... 199 28 659

(51) Int. Cl.$^7$ .............................................. A61N 1/365
(52) U.S. Cl. ....................................................... 607/17
(58) Field of Search ........................................ 607/9, 17

(56) References Cited

U.S. PATENT DOCUMENTS

| 5,360,436 | A | 11/1994 | Alt et al. |
| 5,645,575 | A | 7/1997 | Stangl et al. |
| 5,800,471 | A | 9/1998 | Baumann et al. |
| 5,824,019 | A | 10/1998 | Rueter et al. |
| 5,836,987 | A | 11/1998 | Baumann et al. |

FOREIGN PATENT DOCUMENTS

| DE | 198 04 843 | 8/1999 |
| EP | 0 310 216 | 4/1989 |
| EP | 0 570 895 | 11/1993 |
| WO | 98 14240 | 4/1998 |

*Primary Examiner*—Scott M. Getzow
(74) *Attorney, Agent, or Firm*—Browdy and Neimark

(57) ABSTRACT

An inventive method for determining a variable control parameter for an implantable medical device comprises the following procedural steps:
measuring a physiological base parameter that is significant for the control parameter, after a trigger event has occurred,
determining a measuring-signal curve for the base parameter from the above measuring process,
determining a certain event type of the trigger event,
selecting a reference signal curve in dependence on the determined event type,
comparing the measuring signal curve to the selected reference signal curve,
determining a comparison value that is representative for the difference between the measuring signal curve and the reference signal curve, and
determining the control parameter from the comparison value according to a predefined calculation algorithm.

13 Claims, 2 Drawing Sheets

METHOD FOR DETERMINING A VARIABLE CONTROL PARAMETER FOR AN IMPLANTABLE MEDICAL DEVICE

BACKGROUND OF THE INVENTION

1. Field of the Invention

The present invention relates to a method for determining a variable, especially physiological, control parameter for an implantable medical device, particularly for the heart rate adaptation in a cardiac pacemaker.

2. Background Art

Although the present invention has applications in connection with a variety of implantable medical devices, for purposes of better illustration the background of the invention can be explained based on the example of a cardiac pacemaker.

A modern cardiac pacemaker represents an implantable medical device for which a certain physiological control parameter must be determined and set. This control parameter may be the heart rate, for instance, i.e., the frequency at which the heart beats, if necessary upon delivery of a stimulation pulse by the pacemaker. The heart rate of a pacemaker-supported heart is, accordingly, comparable to the pulse frequency of the healthy heart.

It is well known that the pulse frequency, and accordingly also the optimum heart rate as it is to be generated by a pacemaker, depends on the given current condition of the patient. If the patient is exercising, for example, the heart rate must be adjusted higher than when the patient is resting. At the same time, an increased ejection performance of the heart is attained as well, in addition to an increased heart rate or pulse frequency, due to an increased contractility. A wide-spread heart disorder, in this context, results from the fact that, on one hand the natural rate adaptation of the heart through the sinus node no longer functions, but a natural adaptation of the contraction behavior of the heart to the given current physiological needs of a patient is still present. A heart that adapts in this way changes its contraction behavior, for example by changing its beat volume or its contraction speed. As known from the prior art, this change in the contraction behavior can be measured as the starting parameter, knowing that the contraction behavior is significant for the heart rate. The intracardial impedance, for example, must now be measured with a unipolar measurement as the base parameter for this contraction behavior. This is done by applying, between a so-called tip electrode, in the top of the ventricle, and the casing of the pacemaker, a measuring current, which may consist, for example, of bi-phase rectangular pulses of a width of a few ten microseconds and a repetition frequency of some ten to a few hundred hertz. The change in the intracardial impedance due to a contraction of the heart is based on the changing ratio of high-ohm myocardial tissue to low-ohm blood in the vicinity of the tip electrode. A representative measuring signal curve for the intracardial impedance as the base parameter is obtained from a certain contraction behavior. The intracardial impedance, therefore, depicts the dynamics of the contraction process.

These measured dynamics of the contraction process are used for the rate adaptation in known pacemakers in such a way that an algorithm, which is based on clinical experience and corresponding ratings, is used to calculate the rate. This algorithm refers to the difference between the measuring signal curve of the intracardial impedance and an at-rest impedance curve as the reference signal curve. This at-rest curve is subject to fairly long-term changes, which may occur, for example, as an effect of drugs, or due to changes in the patient's fitness level. In the art, the at-rest curve is therefore continually updated.

As was now determined as the starting point for the development of the present invention, the contraction dynamics vary during different events and successions of events, such as, on one hand, during a natural self-stimulated contraction of the heart and, on the other hand, an atrial stimulation that is generated by the pacemaker. For this reason, a heart rate adaptation could, until now, be performed only for a certain trigger event—for example an atrial and ventricular stimulation of the heart by the pacemaker—based on a single at-rest curve. From a physiological point of view this is insufficient.

SUMMARY OF THE INVENTION

Based on the above, the object of the invention is to improve a method for determining a variable control parameter for an implantable medical device in such a way that different initial situations and the resulting influences on the determination of the parameter are compensated for.

This object is met with a method comprising the following combination of procedural steps:

measuring a physiological base parameter that is significant for the control parameter, after a trigger event has occurred, determining a measuring signal curve for the base parameter from the above measuring process, determining a certain event type of the trigger event, selecting a reference signal curve in dependence on the determined event type, comparing the measuring signal curve to the selected reference signal curve, determining a comparison value that is representative for the difference between the measuring signal curve and the reference signal curve, and determining the control parameter from the comparison value according to a predefined calculation algorithm.

In addition to determining an active physiological control parameter, such as the aforementioned heart rate of a pacemaker, passive control parameters may be determined as well, which are of interest, for example, as diagnostic data for the recognition of transplant rejection reactions, ischemic episodes, effects of drugs, or the early recognition of tachycardias by means of appropriate implantable devices. The selection of possible base parameters is accordingly wide. Besides evaluating a mechanical behavior, such as the contraction of the heart, by measuring the intracardial impedance, an evaluation may also be performed based directly on an electro-medical parameter, such as the intracardial electrogram, the mono-phase action potential, or the evoked response, as the measuring signal curve for a significant physiological base parameter.

The gist of the present invention, in connection with all of the above applications, is the measure of determining certain event types during the performance of the present method for the trigger event that triggers the determination of the variable control parameter, and selecting, in dependence on the determined event type, a reference signal curve that corresponds to this event type. This improves the starting basis for determining the control parameter, and optimizes it for the given prevailing situation.

The invention, which, because of its wide range of medical applications, was described in a very abstract fashion above, will be described in more detail below based on an example embodiment, with reference to the appended drawings.

DESCRIPTION OF THE PREFERRED EMBODIMENT

Figure 1:
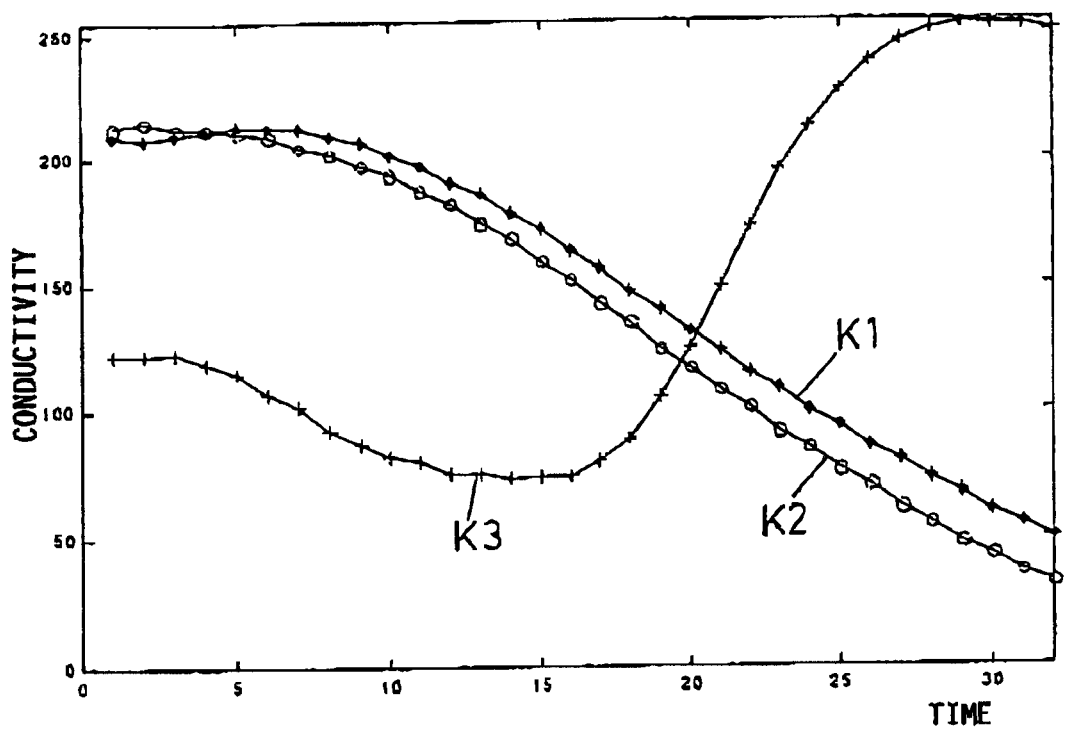
FIG. 1 shows a curve diagram of at-rest impedance curves for different event type sequences.

The inventive method is implemented on a rate-adaptive pacemaker, the microprocessor-based control of which implements this method by means of a process that functions according to a known technical principle. For the rate adaptation—i.e., for the determination of the most optimized heart rate for the patient as it is to be applied by the pacemaker in the case of a stimulation—this variable physiological control parameter is determined according to the method that will be discussed below. The starting point is the measurement of the intracardial impedance of the heart between the cardiac pacemaker electrode, which is anchored at the top of the right ventricle, and the casing of the pacemaker. This means the measurement is performed unipolar, with bi-phase rectangular pulses of a duration of a few ten microseconds and a repetition frequency of a few ten hertz used as the measuring current. This measuring current causes a voltage drop in the region between the tip electrode and the cardiac pacemaker casing, based on the impedance of both, the myocardial muscle tissue, as well as the blood contained in the ventricle. During the contraction of the heart, the ratio between the amount of blood and the amount of muscle tissue changes, which means that the intracardial impedance is significant for the dynamic course of the contraction. The base parameter for the presented method, therefore, is this dynamic intracardial impedance of the heart during a contraction, the behavior of which, in turn, is significant for the heart rate that is to be controlled.

The above fact can be explained from the fact that under physical stress, the patient's heart rate increases on one hand, but on the other hand the contraction behavior of the heart is being changed as well. Conclusions for the heart rate to be adjusted can, therefore, be drawn from the measurement of the contraction behavior of the heart. This is always done starting from an at-rest impedance curve, which can be obtained by averaging across multiple contractions. This at-rest contraction curve represents the reference-signal curve, on the basis of which the heart rate is determined by means of an algorithm that will be explained later.

The reference-signal curve of different successions of trigger events displays significant differences, upon which this invention is based. A trigger event, for the purposes of the presently discussed embodiment, is the actual pacemaker action, which can be related to different type sequences. In a DDD pacemaker, for example, an atrial and ventricular scanning of the heart action is performed, and an atrial as well as ventricular stimulation is delivered as needed. These events are sensed and/or initiated in the right side of the heart. If they are extended to the left side of the heart, the number of possible different events increases accordingly.

Typical pacemaker actions are event sequences of the respective types "atrial stimulation/ventricular stimulation" (abbreviated with Ap/Vp), "atrial stimulation/sensing of a natural ventricular action of the heart" (Ap/Vs), "sensing of a natural atrial action of the heart/ventricular stimulation" (As/Vp), or "sensing of a natural atrial action of the heart/ sensing of a natural ventricular action of the heart" (As/Vs). In the above abbreviations, "A" thus stands for an atrial event, "V" for a ventricular event, "p" (=pace) for a stimulation of the heart by the pacemaker and "s" (=sense) for the sensing of a contraction of the heart by the pacemaker that takes place based on a natural action by the heart, i.e., practically a natural contraction. Incidentally, individual pacemaker actions of the type Ap, As, Vp or Vs, may also be used as a trigger event.

During the development of the present invention it has now been found that the at-rest impedance curves for the different event type sequences Ap/Vp, Ap/Vs, As/Vp and As/Vs discussed above are different. This becomes apparent from FIG. 1:

In this drawing, three measuring curves K1, K2 and K3 have been entered into a time-conductivity diagram, with random units used on the axes. The conductivity qualitatively represents the reciprocal value of the impedance of the heart that is really of interest.

The measuring curves K1, K2 and K3 were determined by averaging multiple pacemaker actions. The measuring curve K1 represents the at-rest curve for the event sequence Ap/Vs. The measuring curve K2 depicts the event sequence As/Vs, and the measuring curve K3 relates to the sequence As/Vp. The measuring curve K3 illustrates that the dynamic contraction of the heart greatly depends on the given heart or pacemaker action. The curve K3—in contrast to the curves K1 and K2—shows a sequence of events during which a ventricular stimulation took place by the pacemaker (event type Vp). The resulting excitation wave, in comparison to the excitation wave from a spontaneous contraction, extends in the opposite direction as reflected by the pattern of the measuring curve K3, which is drastically different in comparison to the measuring curves K1 and K2.

The above illustrates the particular relevance of the procedural step of determining a certain event type for the trigger event that takes place in the pacemaker, and selecting a reference-signal curve in dependence on the determined event type. If the pacemaker has just sensed the event sequence As/Vp (measuring curve K3), it must use this reference curve for the further determination of the heart rate. If the event sequence Ap/Vs was sensed, a curve of the type K1 must be used.

Figure 2:
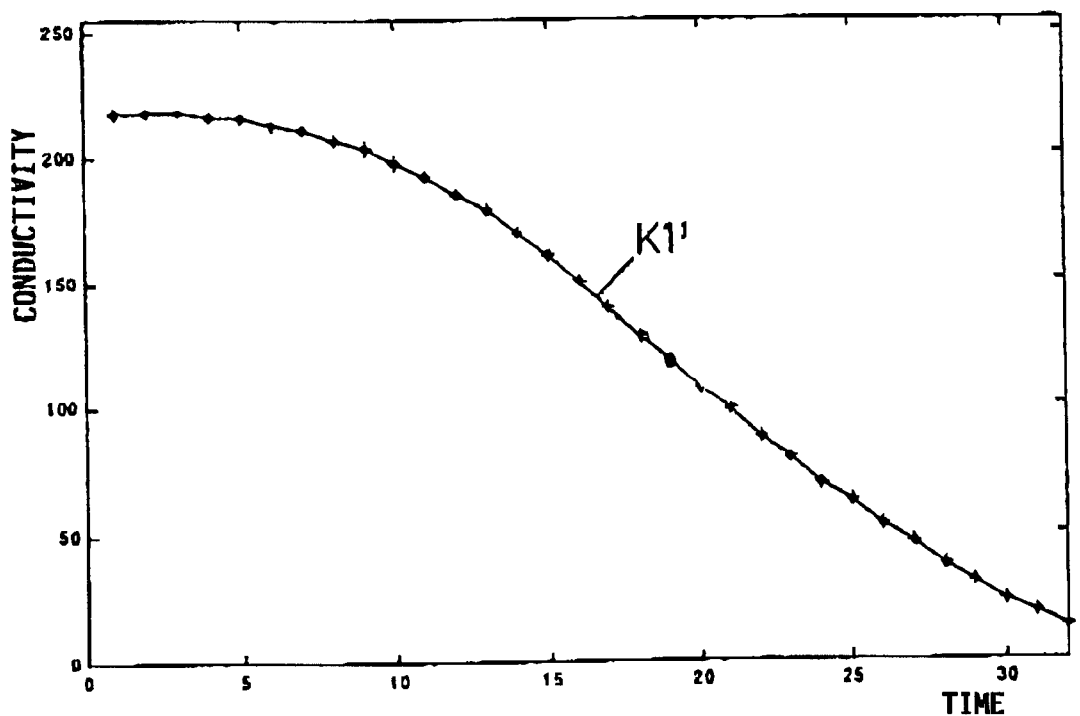
FIG. 2 shows a curve diagram of an impedance curve of a patient under physical stress.
Figure 3:
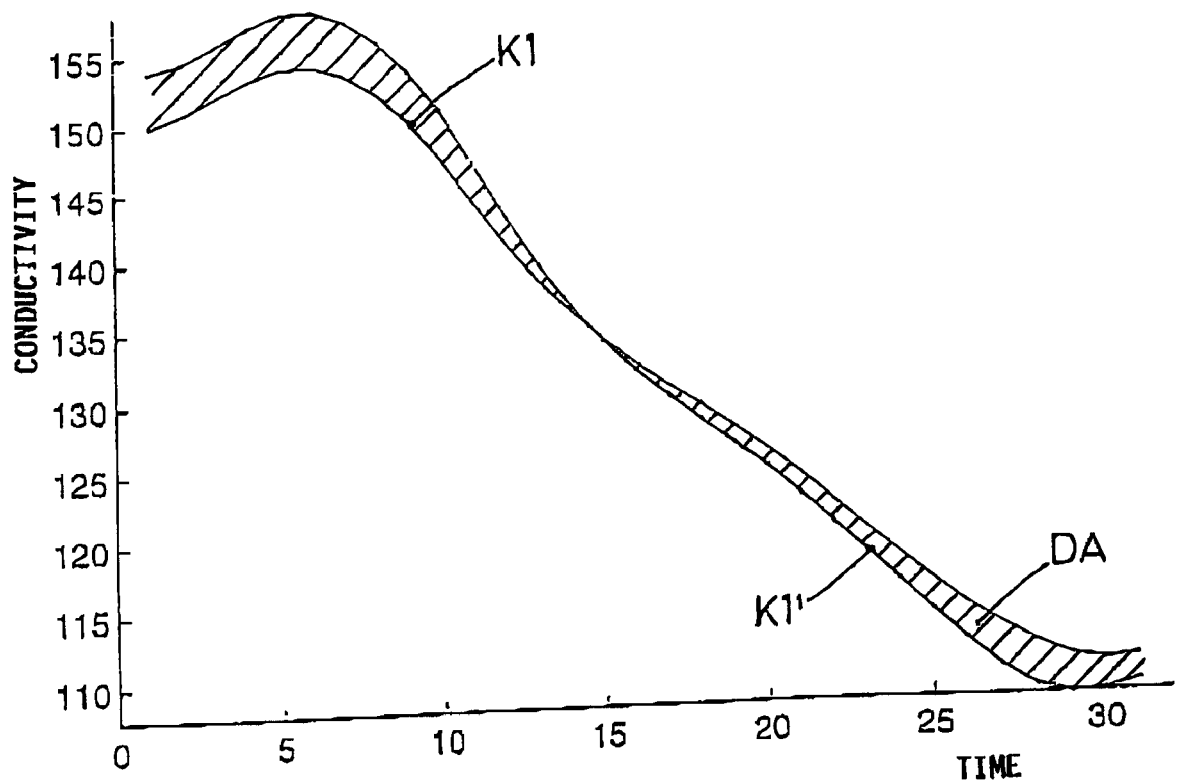
FIG. 3 shows a curve diagram with an at-rest impedance curve and an under-stress impedance curve.

FIG. 2 now shows, analogous to FIG. 1, a measuring signal curve of a patient under physical stress, with the sequence of events Ap/Vs, i.e., "atrial stimulation/sensing of a natural ventricular action of the heart" sensed by the pacemaker as the event type. To this extent, the reference signal curve according to curve K1 in FIG. 1 must be used for the inventive method, and the measuring signal curve according to K1' in FIG. 2 must be compared with this reference signal curve. From this, a comparison value is determined, which is defined by the absolute differential area between the two curves. This can be explained based on the curve diagram in FIG. 3, where the two signal curves K1 and K1' have been entered again in a qualitatively coincident fashion. It becomes clear that a contraction with a large amplitude takes place under physical stress (curve K1'), since the maximum and minimum value of the curve K1' each are above or below the at-rest impedance curve K1. The absolute differential area DA is shown hatched in FIG. 3. In practice it is determined by approximation in such a way that a subtraction between the respective values of the curves K1 and K1' is performed along the signal curves in eight discretely selected comparison points on the time axis; the absolute amounts of the differences are added up and divided by the number of measuring points. This can be expressed with the following evaluation equation:

$$DA = 1/8 \cdot \sum_{i=1}^{8} |K1(i) - K1'(i)|$$

This determined comparison value DA enters into the determination of the control parameter—in the present case the heart rate to be adjusted—based on an algorithm that is predefined in the pacemaker control program.

An algorithm of this type may be implemented, for example, with the following relation:

HR=BR+rf·DA wherein:
 HR=heart rate
 BR=base rate
 rf=response factor
 DA=differential area From the above relation it thus becomes clear that, to determine the control parameter "heart rate HR", the differential area DA is scaled with a response factor rf and the scaled differential area is added to a base heart rate BR as an addend. The base heart rate will be a physiologically sensible value for the heart rate of the patient in resting condition. Based on this value the heart rate is increased under physical stress.

As diagnostic findings have shown, the calibration factors, such as the base rate BR and the response factor rf, like the actual reference signal curves K1, K2, K3, are not static but they can change with differing time constants. To this extent it is advantageous if the relevant known autocalibration routines in common pacemakers cycle through all operating conditions after predefined times, in order to update the parameters. To this extent, the relevant trigger events are forced after predefined time periods. This means that, for example, even if the pacemaker-supported heart continually produces its own natural contraction of the atrium and the ventricle, a stimulation of the atrium, the ventricle, and both parts of the heart is provoked by a corresponding activation of the pacemaker. Based on the event type sequence As/Vs, the event sequences Ap/Vs, As/Vp and Ap/Vp are thus forced. When these events occur, the respective reference signal curves can be recorded and the autocalibration routines that are commonly used with pacemakers can run.

It is furthermore understood that the measures for stabilizing the heart rate as they are known from the pacemaker technology, such as the so-called A-V hysteresis and the atrial overstimulation (so-called A-V scans) can also be used in combination with the inventive method.

What is claimed is:

1. A method for determining a variable control parameter for an implantable medical device, comprising following procedural steps:

measuring a physiological base parameter that is significant for the control parameter, after a trigger event has occurred, determining a measuring signal curve for the base parameter from the above measuring process, determining a certain event type of the trigger event, selecting a reference signal curve in dependence on the determined event type, comparing the measuring signal curve to the selected reference signal curve, determining a comparison value that is representative for a difference between the measuring signal curve and the reference signal curve, and determining the control parameter from a comparison value according to a predefined calculation algorithm.

2. A method according to claim 1, wherein the base parameter is a dynamic intracardial impedance of the heart during a contraction.

3. A method according to claim 2, wherein for different event types, different at-rest impedance curves are selected as the reference signal curve.

4. A method according to claim 3, wherein a comparison value for a difference between the measuring signal curve and the reference signal curve is an absolute differential area between the reference signal curve that was selected based on the event type and the respective measuring signal curve.

5. A method according to claim 4, wherein the reference signal curve and the measuring signal curve are subjected to a subtraction in discretely selected comparison points.

6. A method according to claim 4, wherein the differential area is scaled with a response factor and a scaled differential area is added as an addend to a base heart rate to adapt the heart rate of a pacemaker.

7. A method according to claim 1, wherein the trigger event is a pacemaker action or a succession of pacemaker actions.

8. A method according to claim 7, wherein the pacemaker actions are event sequences (Ax/Vx) of respective types "atrial stimulation/ventricular stimulation" (Ap/Vp), "atrial stimulation/sensing of a natural ventricular action of the heart" (Ap/Vs), "sensing of a natural atrial action of the heart/ventricular stimulation" (As/Vp), or "sensing of a natural atrial action of the heart/sensing of a natural ventricular action of the heart" (As/Vs).

9. A method according to claim 7, wherein the pacemaker actions are events of the respective types "atrial stimulation" (Ap), "sensing of a natural atrial action of the heart" (As), "ventricular stimulation" (Vp), or "sensing of a natural ventricular action of the heart" (Vs).

10. A method according to claim 1, wherein to adapt calibration factors to be applied in the determination of respective comparison values and control parameters, relevant trigger events are forced after predetermined time periods.

11. A method according to claim 1, wherein the measuring signal curves are determined by averaging across multiple measuring processes.

12. An implantable medical device comprising a microprocessor-aided control that implements the method according to claim 1.

13. An implantable medical device in accordance with claim 12, comprising a rate adaptive pacemaker.

* * * * *